(12) United States Patent
Zhao

(10) Patent No.: US 8,771,348 B2
(45) Date of Patent: Jul. 8, 2014

(54) MULTIFOCAL INTRAOCULAR LENS

(75) Inventor: Huawei Zhao, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 641 days.

(21) Appl. No.: 12/254,677

(22) Filed: Oct. 20, 2008

(65) Prior Publication Data

US 2010/0100177 A1    Apr. 22, 2010

(51) Int. Cl.
*A61F 2/16* (2006.01)

(52) U.S. Cl.
USPC .................. 623/6.3; 623/6.31; 351/159.11

(58) Field of Classification Search
USPC .......... 623/6.27–6.31, 6.23–6.24; 351/159.11
See application file for complete search history.

(56) References Cited

U.S. PATENT DOCUMENTS

| | | | | |
|---|---|---|---|---|
| 4,778,462 A | * | 10/1988 | Grendahl | 623/6.27 |
| 4,795,462 A | * | 1/1989 | Grendahl | 623/6.28 |
| 4,881,805 A | | 11/1989 | Cohen | |
| 5,089,024 A | * | 2/1992 | Christie et al. | 623/6.28 |
| 5,096,285 A | | 3/1992 | Silberman | |
| 5,121,979 A | | 6/1992 | Cohen | |
| 5,121,980 A | | 6/1992 | Cohen | |
| 5,129,718 A | | 7/1992 | Futhey et al. | |
| 5,144,483 A | | 9/1992 | Cohen | |
| 5,225,858 A | | 7/1993 | Portney | |
| 5,229,797 A | | 7/1993 | Futhey et al. | |
| 5,589,982 A | | 12/1996 | Faklis et al. | |
| 5,682,223 A | * | 10/1997 | Menezes et al. | 623/6.28 |
| 5,684,560 A | * | 11/1997 | Roffman et al. | 351/160 R |
| 5,748,282 A | | 5/1998 | Freeman | |
| RE36,150 E | | 3/1999 | Gupta | |
| 6,325,510 B1 | | 12/2001 | Golub et al. | |
| 6,536,899 B1 | | 3/2003 | Fiala | |
| 6,557,998 B2 | | 5/2003 | Portney | |
| 6,576,011 B2 | | 6/2003 | Portney | |

(Continued)

FOREIGN PATENT DOCUMENTS

RU    2186417    7/2002

OTHER PUBLICATIONS

Cohen, "Diffractive Bifocal Lens Design", Optom. Vis. Sci 70(6) 461-468, (Jun. 1993).

(Continued)

*Primary Examiner* — Paul Prebilic
(74) *Attorney, Agent, or Firm* — Abbott Medical Optics Inc.

(57) ABSTRACT

The invention provides an IOL, a method of making the IOL, and a method of using the IOL, wherein the IOL includes a central region and an outer region. An ophthalmic lens comprises a central region and an outer region. The central region is disposed about an optical axis and comprises a diffractive pattern having an add power. The central region also has a first power and a second power for visible light. The first power is a power for far focus and the second power equals to the sum of the power for far focus and the add power. The outer region encloses the central region and generally has no multifocal diffractive power. At least a portion of the outer region has a curvature that varies with distance from the optical axis. The outer region may include a peripheral region and at least one intermediate region that encloses the central region, wherein the peripheral region encloses the at least one intermediate region and the at least one intermediate region provides at least one intermediate power that is different from the first power and the second power.

16 Claims, 6 Drawing Sheets

(56) References Cited

U.S. PATENT DOCUMENTS

| | | |
|---|---|---|
| 6,609,793 B2 | 8/2003 | Norrby et al. |
| 6,814,439 B2 | 11/2004 | Portney |
| 6,830,332 B2 | 12/2004 | Piers et al. |
| 6,899,425 B2 * | 5/2005 | Roffman et al. ............... 351/161 |
| 6,951,391 B2 | 10/2005 | Morris et al. |
| 7,025,456 B2 | 4/2006 | Morris et al. |
| 7,073,906 B1 | 7/2006 | Portney |
| 7,093,938 B2 | 8/2006 | Morris et al. |
| 7,188,949 B2 | 3/2007 | Bandhauer et al. |
| 7,381,221 B2 | 6/2008 | Lang et al. |
| 2004/0156014 A1 | 8/2004 | Piers et al. |
| 2006/0066808 A1 | 3/2006 | Blum et al. |
| 2006/0098162 A1 | 5/2006 | Bandhauer et al. |
| 2006/0116764 A1 | 6/2006 | Simpson |
| 2007/0032866 A1 | 2/2007 | Portney |
| 2007/0129803 A1 * | 6/2007 | Cumming et al. ............ 623/6.28 |
| 2007/0258143 A1 * | 11/2007 | Portney ......................... 359/565 |

OTHER PUBLICATIONS

Zhao et al. "The Effect of Chromatic Dispersion on Pseudo Phakic Optical Performance", J Opthalmol. 2007, 91:1225-1229, (May 2, 2007).

Apple et al. "Intraocular Lenses: Evolution Design Complications and Pathology", (1989) William & Wilkins, (Jan. 1989).

U.S. Appl. No. 12/254,710, filed Oct. 20, 2008.

U.S. Appl. No. 12/254,723, filed Oct. 20, 2008.

* cited by examiner

MULTIFOCAL INTRAOCULAR LENS

FIELD OF THE INVENTION

This application relates to lenses that can replace or supplement the lens of a human eye.

BACKGROUND OF THE INVENTION

The prior art discloses intraocular lenses. See for example U.S. Pat. No. 6,536,899 to Fiala; U.S. Pat. No. 6,557,998 to Portney; U.S. Pat. No. 6,814,439 to Portney; U.S. Pat. No. 7,073,906 to Portney; and U.S. Pat. No. 7,093,938 to Morris. U.S. Pat. No. 7,073,906 is directed to an "Aspherical Diffractive Ophthalmic Lens." U.S. Pat. No. 7,093,938 is directed to a "Bifocal Multiorder Diffractive Lenses for Vision Correction."

IOL means Intraocular Lens. D means Diopters. The refractive index of air is 1.000 and of an average human cornea is about 1.376. The optical power of the human cornea is generally about 40 D; of the human lens (relaxed) is generally about 20 D; of an entire human eye is generally about 60 D; and the maximum change in the power of the human eye due to accommodation is generally about 8 D in a young human eye.

The values for peak wavelength sensitivity of the human eye under scotopic conditions is 507 nanometers (nm), and under photopic conditions is 555 nm.

Photopic vision means day time vision. Mesopic vision means evening vision. Iris means the contractile membrane perforated by the pupil, and forming the colored portion of the eye.

As used herein, the term "near vision" means vision produced by an eye that allows a subject to focus on objects that are within a range of about 25 cm to about 40 cm from the subject, or at a distance at which the subject would generally place printed material for the purpose of reading. As used herein, the term "intermediate vision" means vision produced by an eye that allows a subject to focus on objects that are located from about 40 cm to about 2 meters from the subject. As used herein, the terms "far vision" or "distant vision" means vision produced by an eye that allows a subject to focus on objects that are at a distance that is greater than 2 meters, at a distance of 5 meters or about 5 meters from the subject, or at a distance of 6 meters or about 6 meters from the subject. For example, an add power of 1 Diopter is suitable for focusing an object onto the retina that is located at a distance of 1 meter from an emmetropic eye in a disaccommodative state (e.g., with a relaxed ciliary muscle), while add powers of 0.5 Diopter, 2 Diopters, 3 Diopters, and 4 Diopters are suitable for focusing an object onto the retina that is located at a distance of 2 meters, 50 cm, 33 cm, and 25 cm, respectively, from an emmetropic eye in a disaccommodative state. As used herein "far focus", "near focus", and "intermediate focus" means a focus produce at the retina or image plane of a subject eye or a model eye that corresponds to far vision, near vision, and intermediate vision, respectively.

A multifocal optic or lens may be characterized by "base power" and at least one "add power". As used herein the term "base power" means a power (in Diopters) of an optic, or portion thereof, required to provide distant vision or a far focus at the retina of a subject eye when the optic or lens is disposed in the eye. As used herein, the term "add power" means a difference in optical power (in Diopters) between a second power of the optic or lens and the base power. When the add power is positive, the sum of the add power and the base power corresponds to a total optical power suitable for imaging an object at some finite distance from the eye onto the retina. A typical maximum add power for an optic or lens is about 3 Diopter or about 4 Diopters in the plane of the lens, although this number may be as high as 6 or more Diopters (an intraocular lens add power of 4.0 Diopters is approximately equal to an increase in optical power of about 3.2 Diopters in a spectacle lens).

Refraction herein means the change of direction of propagation of light either at a continuous interface between dielectric media having distinct indices of refraction, or bending of light due to a gradient in an index of refraction in the media through which the light propagates.

The pupil of the human eye is generally smaller in photopic than in mesopic (or scotopic) conditions. The majority of middle age people have a pupil that, during day time, is within 1.1 millimeters (mm) of 3.4 mm in diameter, and during evening time is within 1.1 mm of 4.3 mm diameter. During night time, pupil size of middle aged people may range to larger than 5 mm. Pupil size decreases with age. Young people may have a pupil size that is as large as 9 mm.

SUMMARY OF THE INVENTION

It is an object of this invention to provide novel IOLs or other ophthalmic lenses designed to replace the lens of a human eye. In one aspect of the present invention, a novel ophthalmic lens has a clear aperture consisting of a central region and an outer region disposed about an optical axis. The central region is disposed about an optical axis and comprises a diffractive pattern having an add power. The central region has or provides a first power and a second power for visible light. The first power is a power for far focus and the second power equals to the sum of the power for far focus and the add power. The second power may be a power for near or intermediate focus. The outer region encloses the central region and has no multifocal diffractive power. At least a portion of the outer region has a curvature and/or a refractive power that varies with distance from the optical axis. In certain embodiments, the outer region comprises a peripheral region and at least one intermediate region between the central and peripheral regions. The at least one intermediate region encloses the central region. The peripheral region encloses the intermediate regions.

The central region includes features defining a multifocal diffractive pattern. The multifocal diffractive pattern provides a difference between two powers, where the difference is defined as an add power. This add power is generally between 1 D and 6 D and, in some embodiments, is preferably about 3 D, about 3.5 D, or about 4 D, where about means plus or minus 0.25 D.

The central region provides a power for far focus and another power equal to the sum of the power for far focus and the add power. In some embodiments, the other power is preferably the power for near focus. In other embodiments, for example in IOLs that provide some accommodation, the other power may be less than the power for near focus, and hence the add power may be less than the 3 D to 4 D typically used to provide power for near focus.

The powers of the intermediate regions are intermediate between the power for far focus and the sum of the power for far focus and the add power. Each intermediate region may be solely refractive, or it may include a diffractive pattern superposed therein.

Preferably, the power or powers of the peripheral region are equal to at least one of the far focus, the sum of the power for far focus and the add power, and a power less than the power for far focus by 0.5 D, plus or minus 0.3 D. The peripheral region may be solely refractive, or it may include a diffractive pattern superposed therein.

In some embodiments, each region provides a power or powers that are distinct from any power of the regions that are adjacent to that region. Distinct, herein, with respect to power, means a difference of at least 0.25 D. In other embodiments, at least some of the adjacent regions define a smoothly varying change in optical power and/or lens surface curvature as distance increases from the optical axis.

The diameter of the IOL is generally between 4 mm and 9 mm. In some embodiments, the diameter of the IOL is preferably about 4 mm to about 6 mm. About, herein with respect to mm, means plus or minus 0.5 mm.

In some embodiments, the peripheral region provides power solely via refraction.

In some embodiments, each intermediate region provides power solely via refraction.

In some embodiments, the power of a region or portion thereof for far focus is about 20 D and the power for near focus is about 23 D to about 24 D. Herein, with respect to power, about, means plus or minus 0.25 D. In general, the power for far focus is within the range of about minus 20 D to about plus 40 D.

Generally, the peripheral region and each intermediate region each form a closed loop.

The power for far focus and a power for near focus of the central region of the IOL may be provided either entirely by the diffractive pattern or by any combination of the diffractive pattern, refractive surfaces, and an index of refraction gradient in the IOL.

In some embodiments, it is preferable that the central region is as large as or at least as large as the size of the iris in photopic conditions, which on average in patient in the target population is 3.4 mm.

Generally, there are at least two intermediate regions and there may be 3-10 or more intermediate regions. Each intermediate region may form a closed loop, such as an annulus. More particularly, the intermediate regions may have circular symmetry about the optical axis of the lens.

In some embodiments, the refractive power of the intermediate regions, as a function of distance from the optical axis form an "n" shape; form a "u" shape; monotonically increase; or monotonically decrease. Thus, in some embodiments, the intermediate region closest to the central region of the IOL has a power less than the sum of the power for far focus and the add power of the central region and greater than the power of any of the other intermediate regions. In other embodiments, the intermediate region closest to the central region of the IOL has a power greater than the power for far focus and less than the power of any of the other intermediate regions. Likewise, a power of the intermediate region closest the peripheral region may be greater than or less than the powers of any of the other intermediate regions.

In other embodiments, ("u" and "n" shaped) an intermediate region intermediate between the central and peripheral regions, has a power that is less than the powers of any of the other intermediate regions, or greater than the powers of any of the other intermediate regions (bottom of the "u" or top of the "n").

In some embodiments, all of the intermediate regions and the peripheral region provide power solely due to refraction. In other embodiments, all of the intermediate regions and the peripheral region provide power due to both refraction and diffraction patterns.

The refractive power of the intermediate regions may sequentially decrease from the intermediate region closest to the central region of the IOL to the intermediate region farthest from the central region of the IOL.

The power provided to the far focus and the other focus of the central region by the central region may be split evenly.

The diffractive pattern in a central region generally has an add power between about 2 D and 6 D, preferably between 3 D and 4.5 D. Typical prescription tolerances are 0.25 diopters.

The diffractive pattern may be superimposed onto a base curvature to define the add power of the central region of the IOL.

The IOL may have at least one surface that deviates from spherical with aspheric terms designed to correct for the average monochromatic aberrations induced in light passing through an average human cornea. Designing non spherical surfaces of lenses is a well-known technique and can be performed according to different principles. U.S. Pat. No. 5,225,858 provides a description of a multi focal ophthalmic lens having aspheric surfaces, and its teachings are incorporated herein in their entirety. The description of such surfaces is explained in more detail in U.S. Pat. No. 6,609,793. The teachings of U.S. Pat. No. 6,609,793 are incorporated herein in their entirety.

Intermediate and the peripheral region may have a diffractive pattern specifically designed only to compensate for chromatic aberration, as for example described in U.S. Pat. No. 7,188,949, which is incorporated in its entirety herein by reference.

DETAILED DESCRIPTION OF THE EMBODIMENTS

Figure 1:
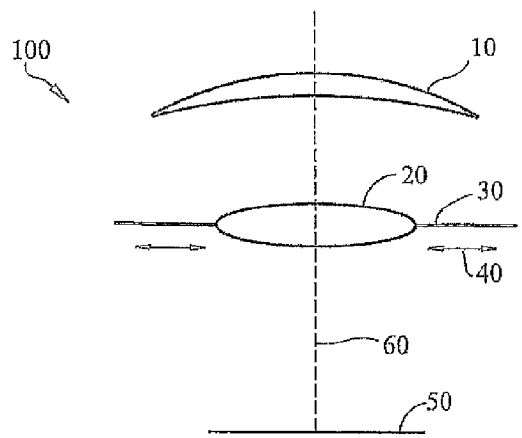
FIG. 1 schematically shows the cornea, pupil, natural lens, and retina of a human eye.

FIG. 1 schematically shows cornea 10, lens 20, iris, 30, and retina 50 of human eye 100. Arrows 40 show that the lens/iris can expand or contract for accommodation. Optical axis 60 is generally perpendicular to the retinal surface, lens, and cornea so that light passing through the optical train is focused in the vicinity of the retina.

Figure 2:
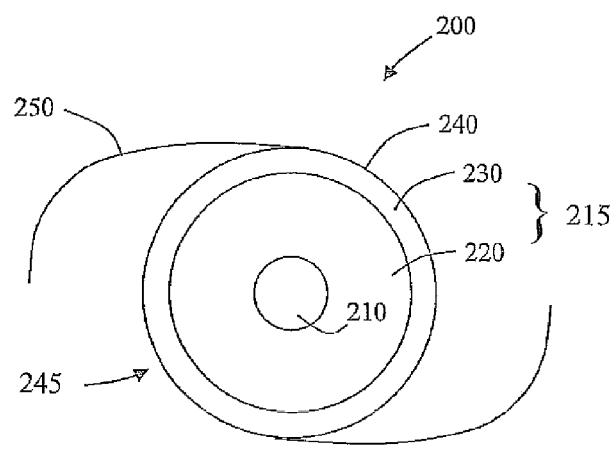
FIG. 2 is schematic and plan view of regions of a first embodiment of an IOL having three regions.

Referring to FIG. 2, in one embodiment, an IOL 200 comprises an optic 245 and a plurality of optional haptics or stabilizers 250. IOL 200 may be configured to replace the natural lens and reside in the eye in the position occupied by the natural lens. Alternatively, IOL 200 may be used in combination with the natural lens and/or another IOL to provide vision to a subject. It will be appreciated that embodiments of the present invention may include an optic such as optic 245 that is adapted for use in other types of ophthalmic lenses (either with or without haptics) such as corneal inlays, corneal onlays, contact lenses, corneal refractive procedures, and the like.

In the illustrated embodiment, IOL 200 includes or has attached thereto stabilizers 250 for stabilizing the IOL in the eye. When expanded, stabilizers 250 project out from the body of IOL 200. Stabilizers 250 may be made of the same material as optic 245 and/or integral therewith. Alternatively, stabilizers 250 may be made of a different material and attached or inserted into optic 245. Stabilizers 250 may be configured according to other forms known in the art and/or to provide other functions besides stabilizing optic 245, for example, to provide accommodative motion or deformation of an optic.

Optic 245 includes central region 210 and outer region 215. Outer region 215 may comprise an intermediate region 220 and a peripheral region 230. Outer region 215 and peripheral region 230 are bounded by an IOL perimeter 240. Optic 245 has a clear aperture that may, for example, be defined by perimeter 240. In some embodiments, perimeter 240 comprises structure and/or means for reducing edge glare, decreasing cell migration on the clear aperture of IOL 200, or the like. In such embodiments, the clear aperture of IOL 200 is generally less than the diameter of perimeter 240.

As used herein, the term "clear aperture" means the opening of a lens or optic that restricts the extent of a bundle of light rays from a distant source that can be imaged or focused by the lens or optic. The clear aperture is usually circular and specified by a diameter. Thus, the clear aperture represents the full extent of the lens or optic usable for forming the conjugate image of an object or for focusing light from a distant point source to a single focus or, in the case of a multifocal optic or lens, to a plurality of foci. It will be appreciated that the term clear aperture does not limit the transmittance of lens or optic to be at or near 100%, but also includes lenses or optics having a lower transmittance at particular wavelengths or bands of wavelengths at or near the visible range of the electromagnetic radiation spectrum.

The central region 210 of optic 245 includes a front surface and an opposing rear surface that are configured to have optical power or power for forming a focused image or spot from light incident thereon. As used herein the terms "power" and "optical power" may be used interchangeably and mean the ability of an optical element or portion thereof to focus incident electromagnetic radiation within the visible waveband, herein referred to as "light" or "white light" and including electromagnetic radiation with a wavelength in a vacuum that is between 390 nanometers and 780 nanometers. The power may be the result of refraction, reflection, and/or diffractive effects produced by the optical element or portions thereof.

In some embodiments, at least one of the surfaces has a curvature that is selected to provide refractive power for forming a far focus. In other embodiments, one or both surfaces is flat or nearly flat, wherein central region 210 may have a refractive power that is due, at least in part, to a refractive index gradient within the material from which optic 245 is formed. In yet other embodiments, one or both surfaces are flat or nearly flat and central region 210 has power for forming a focus based diffractive effects.

Central region 210 also includes a diffractive pattern that provides one or more add powers for light incident thereon. The add power may be selected to provide power for a near focus (e.g., for near vision) and/or an intermediate focus (e.g., for intermediate vision). The diffractive pattern may be imposed on, added to, or combined with a base curvature or base profile on the front and/or rear surfaces of central region 210. As used herein, a "base curvature" or "base profile" is the curvature or profile of a surface that primarily defines a refractive power of that surface. The base curvature or profile may be altered by the inclusion of a diffractive pattern or profile that is configured to provide a diffractive power.

The add power for central region 210 may be produced by a first diffractive order for light incident on optic 245. Alternatively, the add power may be produced by a difference in power between two successive diffractive orders having a relatively large amount of energy, for example, by a difference between the powers of a second diffractive order and a first diffractive order, a third diffractive order and a second diffractive order, a zeroth diffractive order and a minus one diffractive order, or the like.

One or more add powers may be used to produce one or more additional and distinct foci, for example, to provide power for a near focus and/or an intermediate focus. The add power is generally between 1 D and 6 D and, in some embodiments, is preferably about 3 D, about 3.5 D, or about 4 D, where about means plus or minus 0.25 D. In other embodiments, two or more foci are produced that are not distinct. For example, the add power may be between about 0.5 D and about 2.0 D and selected to produce an extended depth of focus, for example, as disclosed in co-pending U.S. patent application Nos. 60/968,250 and 12/120,201, which are herein incorporated by reference.

Thus, central region 210 forms a multifocal diffractive optic region having multifocal diffractive power that may be selected to provide power for far focus, and at least one additional focus that is the sum of far focus power and at least one add power. As used herein, the term "multifocal diffractive power" means an arrangement of zones (e.g., formed by diffractive echelettes disposed on a surface of an optic, a variation in material refractive index, or similar means) that produces two or more distinct foci or diffractive powers within the visible range of the electromagnetic radiation spectrum through constructive interference between zones.

The diffractive pattern of central region 210 may consist of a series of radial rings, "zones", or echelettes of decreasing width. The add power for near field focus is generally determined by the diameters of the diffractive zones. The light distribution of the diffractive bifocal lens may be controlled by the step height and the shape of the individual diffractive zones. There are several known techniques to modify the light distribution of multifocal diffractive lenses by reducing the step height of the diffractive pattern in the direction towards the periphery of lens. U.S. Pat. No. 4,881,805 suggests different routes to use different echelette depths to vary the light intensity among the different foci of a multi focal lens. U.S. Pat. No. 5,699,142 discloses a multi focal intraocular lens with a diffractive pattern having an apodization zone that gradually shifts the energy balance from the near focus to the far focus. The apodization zone is constructed so that the echelettes of the diffractive pattern have gradually reducing depth as one moves towards the lens periphery. By making an appropriate adjustment of the step height (echelette depth), a desired distribution of intensity between the two foci of a bifocal lens can be obtained. Typically, the light distribution of a bifocal diffractive pattern is set to 50 percent to far field focus and 50 percent to at add power (near field). The diffractive pattern may be formed on either surface or at an intermediate dielectric interface in the lens.

The diffractive pattern can be described using conventional equations. For example, as discussed in Cohen, "Diffractive bifocal lens design", Optom. Vis. Sci. 70(6): 461:8 (1993), which describes a diffractive profile with the equation: $S_d(r) = h*\{N-r^2/w^2\}$ wherein r is the distance from the optical axis; h is the maximum profile height (step height); N is the zone number; and w is the width of the first zone. Other equations are also possible. The background section of U.S. Pat. No. 7,073,906 contains a description of the effect of parameters of the diffractive patter on light distribution and focal power. The teachings of U.S. Pat. No. 7,073,906 are incorporated herein by reference.

Outer region 215, which includes intermediate and peripheral regions 220, 230 in the illustrated embodiment, may be configured to include a multifocal optic region with multifocal refractive power. Additionally or alternatively, outer region 215 may include a monofocal optic region. The monofocal optic region may have an extended depth of focus, for example, a depth of focus that is larger that that of a spherical lens having the same or substantially the same focal length as that of outer region 215. Outer region 215 may produce variations in power by varying a surface curvature and/or a local refractive index of the material from which IOL 200 is made. Outer region 215 does not generally include a diffractive pattern or echelettes that have multifocal diffractive power for visible light; however, may include a diffractive pattern configured to produce a single focus or power for white light, for example, configured to reduce or eliminate a chromatic aberration of optic 245 and/or an eye into which IOL 200 is placed.

Advantageously, it has been found that the combination of a multifocal diffractive pattern in central region 210 and a multifocal or extended depth of focus refractive configuration in intermediate region 220 or peripheral region 230 are able to provide, in a single lens, distinct benefits of both refractive and diffractive multifocal lenses. In particular, for a smaller pupil sizes (e.g., under photopic lighting conditions), the multifocal diffractive pattern of central region 210 provides power for both far focus and near focus that is relatively distinct and sharp as compared to a refractive multifocal. Under such conditions, it has been found that there is less need to provide intermediate vision, as such, since smaller pupil sizes inherently have relatively large depths of focus. In addition, under mesopic and/or scotopic lighting conditions, a refractive multifocal configuration in intermediate region 220 or peripheral region 230 favorably provides advantages such as the ability of provide at least some intermediate vision, the ability to reduce the effects of halos, and more flexibility in distributing the amount of energy in the near, intermediate, and far foci as the pupil diameter increases.

In certain embodiments, the multifocal diffractive pattern of central region 210 is disposed on a common surface with a refractive multifocal pattern located within intermediate region 220 and/or peripheral region 230. The patterns may be disposed an either an anterior or posterior surface of optic 245. In other embodiments, the multifocal diffractive pattern of central region 210 is disposed on an opposite surface with a refractive multifocal pattern located within intermediate region 220 and/or peripheral region 230.

Intermediate region 220 and/or peripheral region 230 may include a monofocal diffractive pattern, for example, to at least partially compensate for a chromatic aberration of at least one of the IOL and an eye into which the IOL is to be placed. In other embodiments, optic 245 includes a transition region (not shown) disposed between central region 210 and outer region 215 that includes multifocal diffractive power, for example, a diffractive pattern configured reduce the effect of halos that is similar to that disclosed in U.S. Pat. No. 7,188,949.

In some embodiments, at least a portion of outer region 215 has a curvature and/or power that varies with distance from the optical axis. The variation in the curvature and/or power of outer region 215 as a whole is such that the power variation of outer region 215 with distance from the optical axis is greater than that of the power variation of a spherical IOL having a paraxial power equal to the first power of the central region. In other words, the power variation of outer region 215 is greater than that produce by the spherical aberrations of a spherical lens having a base power to provide far focus and/or equal to the base power of central region 210 of IOL 200. The power variation of outer region 215 may be either positive or negative as a function of distance from the optical axis. Portions of the power variation may be negative with increasing distance from the optical axis, for example to compensate for, reduce, or eliminate a spherical aberration of the lens 200 and/or of an eye. In some embodiments, the overall power variation may be positive with increasing distance from the optical axis, for example, to provide a multifocal capability, while the power variation of selected portions may be negative (see, for example, U.S. Pat. No. 5,225,858).

In some embodiments, portions of outer region 215 have a power that monotonically increases or decreases as the distance from the optical axis increases. In other embodiments, portions of outer region 215 have a constant power or curvature as the distance from the optical axis increases, for example, to increase the amount of energy contained in a particular focus of the eye as the diameter of the pupil increases under lower lighting conditions. Outer region 215 is generally configured to provide two or more distinct foci (e.g., to provide power for far focus and near focus, or for far focus and intermediate focus). Alternatively, at least portion of the outer region may be configured to provide a single focus with an extended depth of focus, for example, an extended depth of focus as compared to a reference lens having a single power equal to a power of the outer region or some portion of the outer region.

Outer region 230 may be configured to provide power for near focus, far focus, or both near and far foci. It has been found that the intermediate region 220 may be advantageously configured to reduce the effects of halos produced by the multifocal diffractive pattern of the central region 210. Additionally or alternatively, the intermediate region 220 may be configured to reduce the sensitivity of IOL 200 to tilt and/or decentration that can occur when IOL 200 is implanted in the eye of a subject. For example, intermediate region 220 may be configured like or similar to the intermediate zone disclosed in U.S. Pat. No. 7,381,221, which is herein incorporated by reference in its entirety. In such embodiments, intermediate region 220 may have a relatively small radial width, for example, a radial width that is less than a radial width of central region 210 and/or peripheral region 230.

It will be appreciated that the advantages discussed above in relation to IOL 200 may apply to other embodiments of the present invention disclosed herein. IOL 200 and the other IOLs disclosed herein may be composed of materials disclosed in RE36,150, which is herein incorporated by reference in its entirety. Alternatively, the IOL may comprise any material suitable for implantation within the eye. Example of such materials are acrylics and silicones. These materials are known in the art. See for example table 1 in Zhao et al, "The Effect of Chromatic Dispersion on PseudoPhakic Optical Performance", J. Ophthalmol 2007; 91:1225-1229, or David J. Apple, et al., Intraocular Lenses: Evolution, Design, Complications, and Pathology, (1989) William & Wilkins.

At least portions of outer region 215 may have only a single power that is intermediate between the power for far focus and the sum of the power for far focus and an add power for near or intermediate vision. At least portions of outer region 215 may have a surface defining a bifocal or multifocal pattern produced by refraction and/or diffraction, in which case the at least portions have two or more different powers associated with it. In such embodiments, these powers may be limited to be intermediate powers between the power for far focus and the sum of the power for far focus and the add power.

Figure 3:
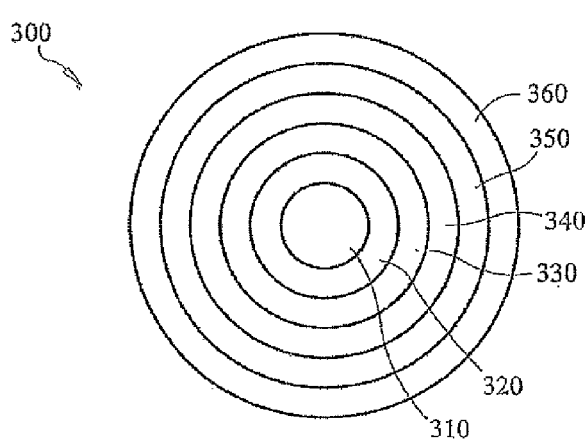
FIG. 3 is a plan view of regions of a second embodiment of an IOL having six regions, with four intermediate annular regions and a peripheral annular region each having an equal annular extent in the radial direction.

FIG. 3 shows in plan view IOL 300 having central region 310, intermediate regions 320, 330, 340, 350, and peripheral region 360. Each of regions 320-360 define annular regions. Each annular region 320-360 has the same radial extent form its inner radius to its outer radius, as any other annular region. Intermediate region 320 is adjacent central region 310. In some embodiments, the intermediate regions provide power solely via refraction, and the power of the intermediate regions monotonically increase from outermost intermediate region 350 to the innermost intermediate region 310. The powers of the intermediate regions are bounded by the two (or two primary) powers provided by the central region. Peripheral region 360 generally provides power solely via refraction and provides the power of the far focus.

Figure 4:
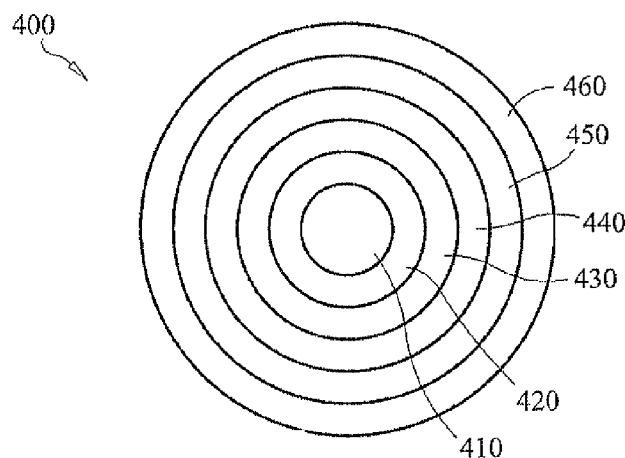
FIG. 4 is a plan view of regions of a third embodiment of an IOL having six regions each having equal area.

FIG. 4 shows a plan view of IOL 400 having central region 410, intermediate regions 420, 430, 440, and 450, and peripheral region 460. Each one of intermediate regions 420-450 and peripheral region 460, in a projection onto a plane perpendicular to the optical axis, have the same surface area. Central region 410 has a surface that includes a diffractive pattern providing add power. Annular regions 420-450 provide powers intermediate between the power for far focus and the sum of the power for far focus and the add power. Peripheral region 460 provides the power for far focus. Alternatively, each annular region 420-460 may have a predetermined radius or area that is selected to provide a particular distribution of near, intermediate, and far vision, for example, as a function of pupil size or lighting conditions.

Reference to upper and lower sides, or front or back sides, of an IOL herein does not imply a particular orientation of sides of the IOL when implanted in a human eye.

Figure 5:
FIG. 5 is side sectional view of a first alternative configuration of the first embodiment in which the central region has no refractive power.

FIG. 5 shows a cross section of IOL 500 having a central region 502, an intermediate region 504, and a peripheral region 506. Central region 502 includes diffractive pattern 570. Central region 502 is delimited by a surface 510 on an upper side of IOL 500 and a surface 560 on a lower side of IOL 500. Surface 510 is defined by a flat base curvature with a diffractive pattern 570 imposed upon the flat base curvature. Diffractive pattern 570 provides both the power of far focus, and power equal to the sum of the power for far focus and the add power. In some embodiments, diffractive pattern 570 is structured to provide equal light intensities to both foci. In the illustrated embodiments surfaces 510, 560 are flat; however, one or both surfaces 510, 560 may have a curvature. For example, one or both surfaces 510, 560 may be curved to provide a refractive power that is combined with the diffractive power provided by diffractive pattern 570.

Intermediate region 504 is delimited by surfaces 520 on an upper side and 550 on a lower side of the IOL. One or both of surfaces 520 and 550 are generally curved and may be designed to at least provide a focal power intermediate between IOL 600's power for far focus and the power equal to the sum of the power for far focus and the add power. Peripheral region 506 is delimited by surface 530 on the upper side of IOL 500 and surface 540 on the lower side of IOL 500. One or both of surfaces 530 and 540 are generally curved and designed to provide a power for at least far focus.

Figure 6:
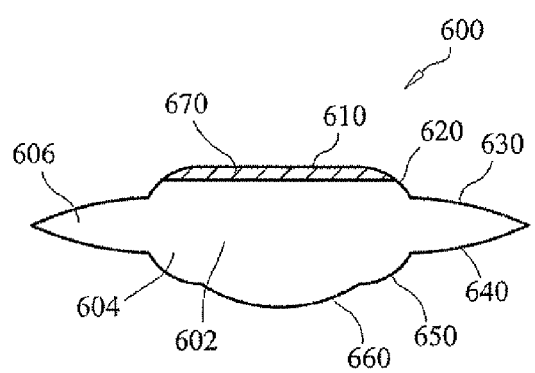
FIG. 6 is a side sectional view of a second alternative configuration of the first embodiment in which the central region has mixed refractive and diffractive power.

FIG. 6 show a cross section of IOL 600 having a central region 602, an intermediate region 604, and a peripheral region 606. Central region 602 includes diffractive pattern 670. Central region 602 is delimited by surface 610 on an upper side of IOL 600 and surface 660 on a lower side of IOL 600. Surface 660 is non-flat. Surface 660 has a curvature that provides a power that provides at least a portion of the total IOL power for far focus. Surface 610 is defined by a flat base curvature with a diffractive pattern imposed upon the flat base curvature. Diffractive pattern 570 provides that portion of the total power for far focus of IOL 600 not provided by surface 660, and an add power, so that the total power of the IOL in central region 602 provides both the power for far focus and the power for the sum of the power for far focus and the add power. Diffractive pattern 670 may be structured so that central region 602 provides equal light intensities to both foci.

Intermediate region 604 is delimited by surfaces 620 on the upper side and 650 on the lower side of IOL 600. One or both of surfaces 620 and 650 are curved and designed to provide a focal power intermediate between IOL 600's power for far focus and sum of the power for far focus and the add power. Peripheral region 606 is delimited by surface 630 on the upper side of IOL 600 and surface 640 on the lower side of IOL 600. On or both of surfaces 630 and 640 are curved and designed to provide the power of the far focus.

In some embodiments, surface 510 of IOL 500 or surface 610 of IOL 600 are curved so as to contribute to the power of the far focus. It will be appreciated that any of the surfaces 510, 560, 610, or 660 may have an aspheric profile that is configured to correct an aberration, such as a spherical aberration, of the IOL and/or eye into which the IOL is implanted. Additionally or alternatively, any of the surfaces 510, 560, 610, or 660 may have a profile that provides one or more refractive powers within the central region of the lens.

Figure 7:
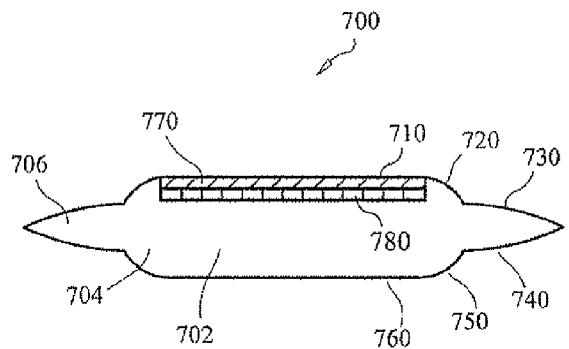
FIG. 7 is a side sectional view of a third alternative of the first embodiment in which some of the refractive power is provided by an index gradient.

FIG. 7 shows a cross section of IOL 700 having a central region 702, an intermediate region 704, and a peripheral region 706, similar to the regions shown in FIGS. 5 and 6. FIG. 7 shows surfaces 710-760, which are similar to the surfaces shown in FIGS. 5 and 6. In contrast to FIGS. 5 and 6, FIG. 7 shows an upper portion of central region 704 having material defining an index of refraction gradient 780 (illustrated by spaced vertical lines). Index of refraction gradient 780 provides a refractive power to central region 702 such that the combined power of gradient 780 and diffractive pattern 770 provide the power for far focus and a power equal to the sum of the power for far focus and the add power, to central region 702. Use of gradient 780 instead of a curved refractive surface allows a thinner IOL to provide the vision correction. Gradient 780 may extend over a limited axial portion of central region 702 (including or excluding diffractive pattern 770) or through the entire axial extent or substantially the entire axial extent of central portion 702 (e.g., excluding diffractive pattern 770).

Figure 8:
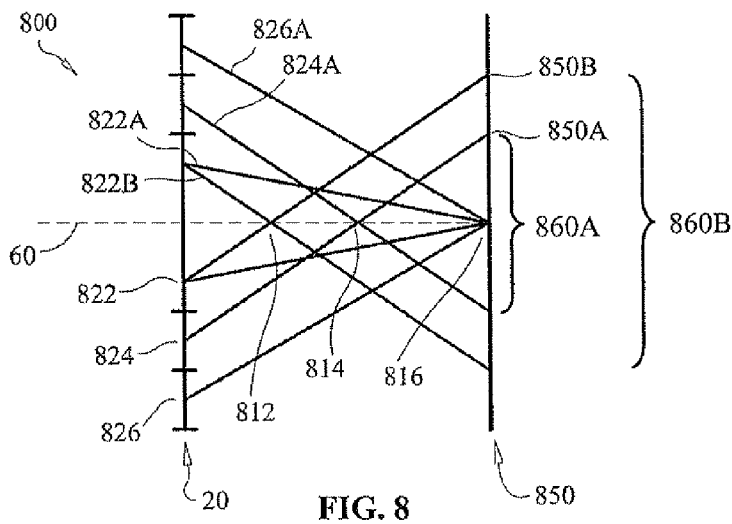
FIG. 8 is a schematic of IOL 800 showing focal points and halo edges.

FIG. 8 schematically shows, in side sectional view in a plane containing the optical axis, an IOL 800 configured to reduce the effects of halos. The IOL 800 focuses incident light onto a retinal plane 850 and includes central region 822, intermediate region 824, and peripheral region 826. FIG. 8 shows rays for the focus of a point object source at an infinite or large distance from the eye and parallel to the optical axis. Ray 826A propagates from the periphery of peripheral region 826 to focal point 816 on retinal plane 850. Ray 824A propagates from intermediate region 824 to focal point 814. Focal point 814 is intermediate between far focal point 816 and near focal point 812. Ray 822A propagates from central region 822 to focal point 816. Ray 822B also propagates from central region 822 to near focus focal point 812. Under the lighting conditions shown in FIG. 8, light focused to focal points 812 and 814 form a halo pattern comprising two distinct halos or disc of light on retinal plane 850. A first halo 860A has an outer edge 850A and comprises light incident on intermediate region 824 that is focused to focal point 814. A second halo 860B has an outer edge 850B and comprises light incident on central region 822 that is focused to focal point 812. In general, the light in each halo 860A, 860B is uniformly or nearly uniformly distributed within each halo. It can be seen in FIG. 8 that light from both focal points 812, 814 illuminates the portion of retinal plane 850 enclosed by halo edge 850A; however, only light from focal point 812 illuminates the portion of retinal plane 850 between halo edge 850A and halo edge 850B. Thus, the intensity of light within outer edge 850A will be higher than the intensity of light between halo edge 850A and halo edge 850B, so that there is a decrease in the intensity of light from the central portion of the halo pattern to the periphery of the halo pattern. It has been found that this type of light distribution within a halo pattern at the retinal plane 850 is less bothersome to a subject than a halo pattern in which light is uniformly distributed over the entire halo to form a sharp demarcation of light intensity at the outer edge of the halo pattern. In some embodiments, one or more additional intermediate regions of the IOL 800 may be configured to provide additional intermediate focal lengths or powers, thereby creating an overall halo pattern with a gradual decrease in the intensity of light from the central portion of the overall halo pattern to the periphery of the overall halo pattern.

Figure 9:
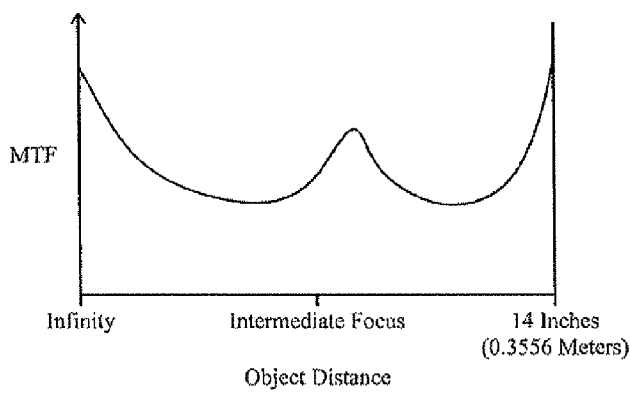
FIG. 9 is a schematic of MTF versus object distance for IOL 800, like IOLs 200, 500, 600, 700, that have three regions including one intermediate region.

FIG. 9 schematically shows an exemplary plot of MTF (for example at 50 lines per millimeter) on the Y axis versus object distance on the X axis for the IOL 800 shown in FIG. 8 when all zones 822, 824, 826 are exposed (e.g., under mesopic or scotopic lighting conditions). Under these conditions, MTF is maximal for objects at infinity (e.g., focal point 816 located on retinal plane 850), at an intermediate distance corresponding to the focal length of the intermediate region (e.g., focal point 814 located on retinal plane 850), and at the near focal length distance (e.g., focal point 812 located on retinal plane 850).

EXAMPLE 1

Mathematical Model of a Lens Having the Following Parameters

In this example, radial distances are defined by a projection onto a plane perpendicular to the optical axis and all aspherical terms were set zero. the IOL material's refractive index is 1.47. IOL lens material corresponds to the commercial product named Sensar, which has a composition described in RE36,150. The IOL has 5 distinct regions. The model lens has an anterior surface with regions defined as follows.

The first region is circular, has an anterior surface radius of 1.7 mm, and its anterior surface has a radius of curvature of 12.2900 mm. The thickness of the central first region is 1 mm.

The second region is annular, has an inner radius of 1.7 mm and an outer radius of 2 mm, and its anterior surface defines a radius of curvature of 9.7248 mm.

the third region is annular, has an inner radius of 2 mm, an outer radius of 2.3 mm, and its anterior surface defines a radius of curvature of 10.4352 mm.

The fourth region is annular, has an inner radius of 2.3 mm, an outer radius of 2.6 mm, and its anterior surface defines a radius of curvature of 11.2575 mm.

The firth region is annular, has an inner radius of 2.6 mm, an outer radius of 3 mm, and its anterior surface defines a radius of curvature of 13.2084 mm.

The model lens has a posterior surface with base curvature having a single radius of curvature of 15.4772 mm. the posterior surface in a circular region about the optical axis extending to radius of 1.7 mm, and is defined by a diffractive pattern imposed on the base curvature. The diffractive pattern provides an add power of 4 D.

Figure 10:
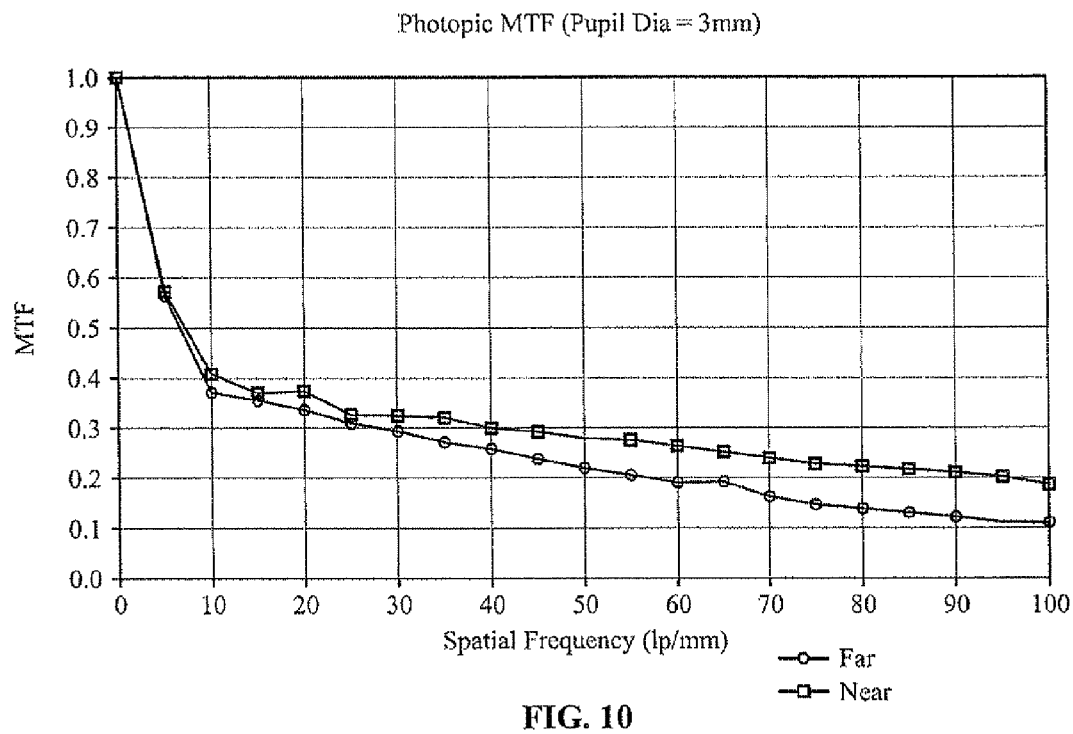
FIG. 10 is a plot of calculations of MTF versus spatial frequency of far and near focus for a pupil diameter of 3 mm and photopic conditions, for example 1.
Figure 11:
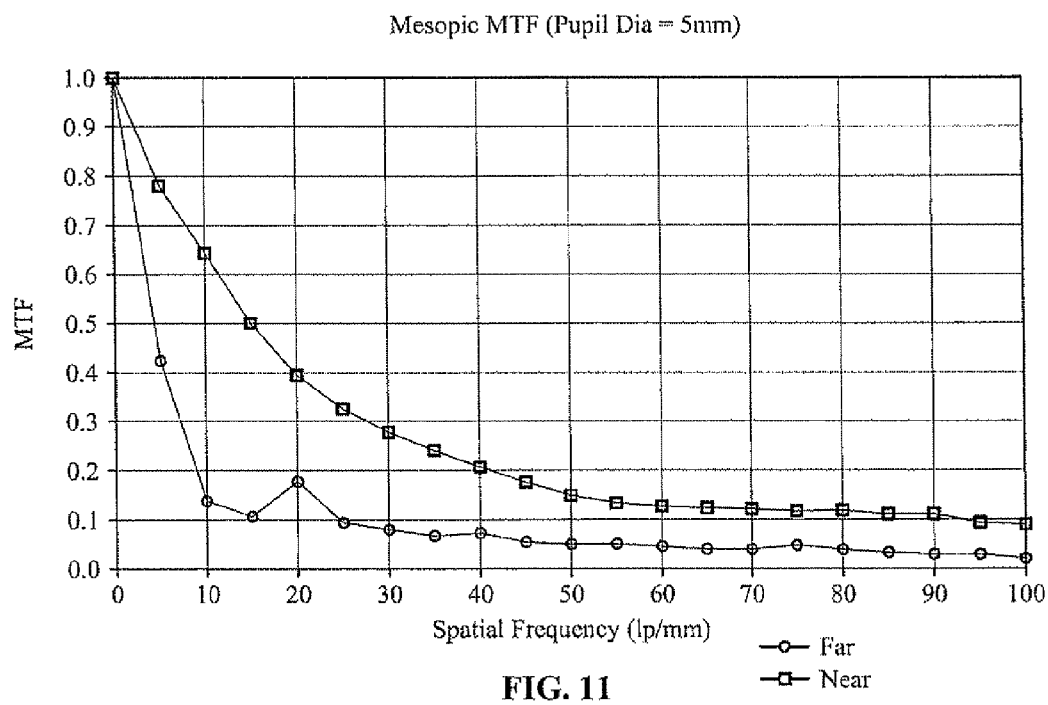
FIG. 11 is a plot of MTF versus spatial frequency of far and near focus for a pupil diameter of 5 mm and mesopic conditions, for example 1.

FIGS. 10 and 11 show data for calculations of Example 1. FIG. 10 simulates effectiveness of the IOL of Example 1 for photopic conditions. FIG. 10 shows a plot of mean transfer function versus spatial frequency in lines per millimeter, along the optical axis, for an eye having a 3 mm diameter pupil. FIG. 10 shows calculation data for far focus with circles, and for near focus with squares. Referring to FIG. 10, it is seen that in certain embodiments an IOL is able to provide a MTF of at least 0.2 at a spatial frequency of 50 lp/mm for a pupil diameter of 3 mm. With further reference to FIG. 10, it is seen that in certain embodiments an IOL is able to provide a MTF of at least 0.1 at a spatial frequency of 100 lp/mm for a pupil diameter of 3 mm. In such embodiments, the IOL provides functional vision for both near and distant object for a pupil diameter of 3 mm, for example, providing a visual acuity of at least 20/20 based on the standard Snellen test for visual acuity.

FIG. 11 simulates effectiveness of the IOL of Example 1 for scotopic conditions. FIG. 11 shows a plot of mean transfer function versus spatial frequency in lines per millimeter, along the optical axis, for an eye having a 5 mm diameter pupil. FIG. 11 shows calculation data for far focus with circles, and for near focus with squares. Referring to FIG. 11, it is seen that in certain embodiments an IOL is able to provide a MTF of at least about 0.05 at a spatial frequency of 50 lp/mm for a pupil diameter of 5 mm. In such embodiments, the IOL provides functional vision for both near and distant object for a pupil diameter of 5 mm, for example, providing a visual acuity of at least 20/40 based on the standard Snellen test for visual acuity.

Interestingly, the IOL of Example 1 is able to provide near vision visual acuity that is even better than the distant vision visual acuity for pupil diameters of both 3 mm and 5 mm, as evidenced by the higher visual acuity shown in FIGS. 10 and 11 for near vision at 50 lp/mm and 100 lp/mm. In other embodiments, the design of Example 1 may be modified to provide a predetermined relative performance in terms of visual acuity between near vision and distant vision, depending on the needs or preferences of the designer, practitioner, or patient. For example, the IOL design may be adjusted so that the visual acuity at 50 lp/mm and/or 100 lp/mm is greater for distant vision than for near vision (based on a pupil diameter of 3 mm and/or 5 mm). Alternatively, the IOL design may be adjusted so that the visual acuity at 50 lp/mm and/or 100 lp/mm is about the same for both distant vision and near vision (based on a pupil diameter of 3 mm and/or 5 mm).

Referring to FIGS. 12-17, other embodiments of an IOL will be discussed. FIGS. 12-17 show power versus radial distance from optical axis for IOLs each having six regions. the six regions are each numbered along the x axis. Region 1 is the central region. Region 6 is the peripheral region. Regions 2-5 are the intermediate regions. The y axis shows power of each region. The central region is the first region, which includes the bifocal diffractive pattern.

FIGS. 12-17 show add power for the central region (region 1), and some cases for the peripheral region (region 6), that is configured to provide near vision, for example, an add power of 3 D or 4 D. In some embodiments the central and/or peripheral region may have a lower add power, such as 1 D or 2 D, for example, to provide an extended depth of focus and/or distant plus intermediate vision. Region 1 of each IOLs of FIGS. 12-16 may have the same extent as region 1 of any of the other IOL's within this group. Similarly, region 2 of each IOLs of FIGS. 12-17 may have the same extent as region of any of the other IOL's within this group. This may also apply to regions 3-6.

Figure 12:
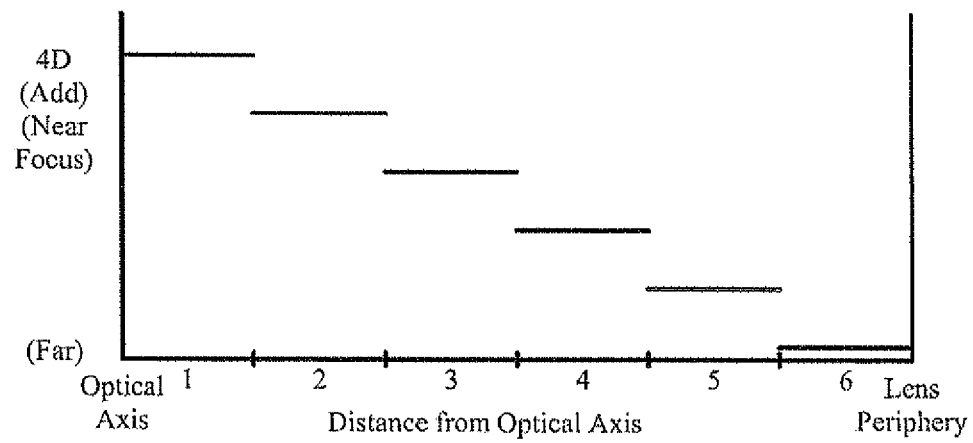
FIG. 12 is a plot of IOL power versus distance from optical axis for an IOL having six regions.

FIG. 12 shows power of an IOL embodiment in which the power outside the central region monotonically decreases from the higher power of the central region with increasing distance from the central region. In this IOL, the peripheral region has only the power for far focus.

Figure 13:
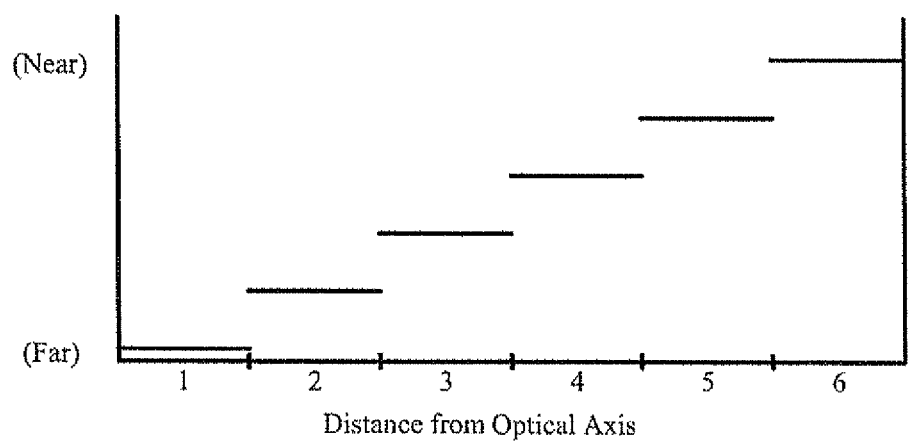
FIG. 13 is a plot of IOL power versus distance from optical axis for another IOL having six regions.

FIG. 13 shows power of an IOL embodiment in which power of each region monotonically increases with increasing distance from the central region. In this IOL, the peripheral region has a power equal to the sum of the power for far focus and the add power.

Figure 14:
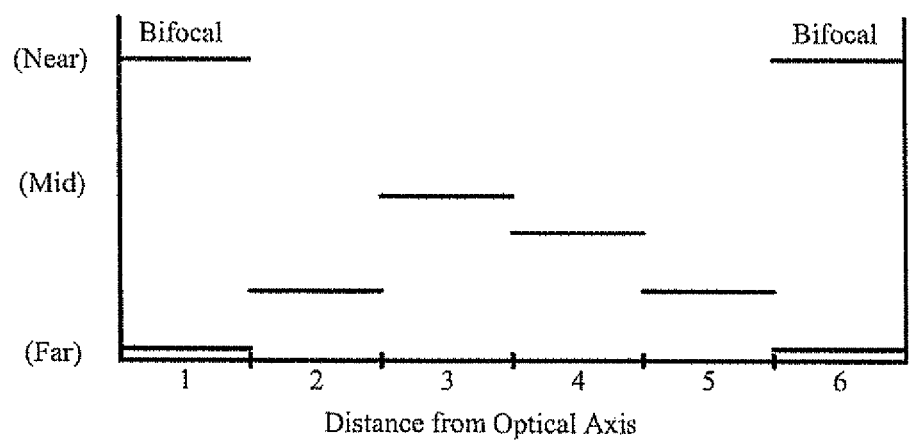
FIG. 14 is a plot of IOL power versus distance from optical axis for another IOL having six regions.

FIG. 14 shows power of an IOL embodiment in which power in the intermediate regions forms a "n" shape as a function of distance from the central region. In this IOL, the peripheral region has two powers; the power for far focus and the sum of that power and the add power. The peripheral region structure is useful if improved distance and near vision are desired for low light conditions.

Figure 15:
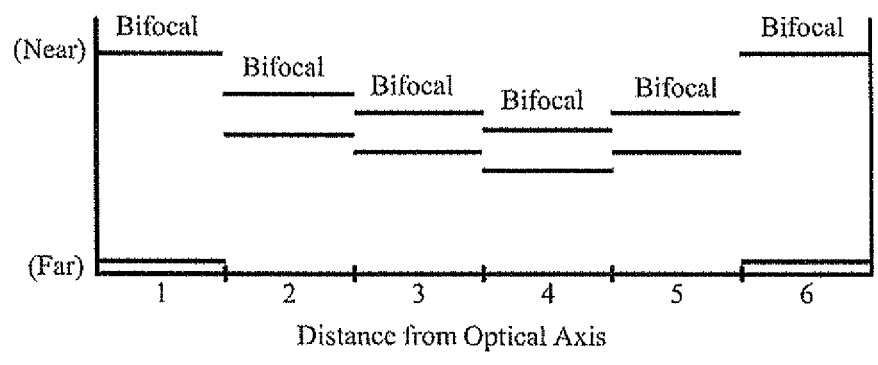
FIG. 15 is a plot of IOL power versus distance from optical axis for another IOL having six regions.

FIG. 15 shows power of an IOL embodiment in which power in the intermediate regions forms a "u" shape as a function of distance from the central region, and in which all six regions include a diffraction pattern so that each region provides two foci. This IOL provides more foci for low light conditions relative to embodiments having mainly refractive only regions, and therefore this IOL should provide more and therefore weaker and less noticeable halos.

Figure 16:
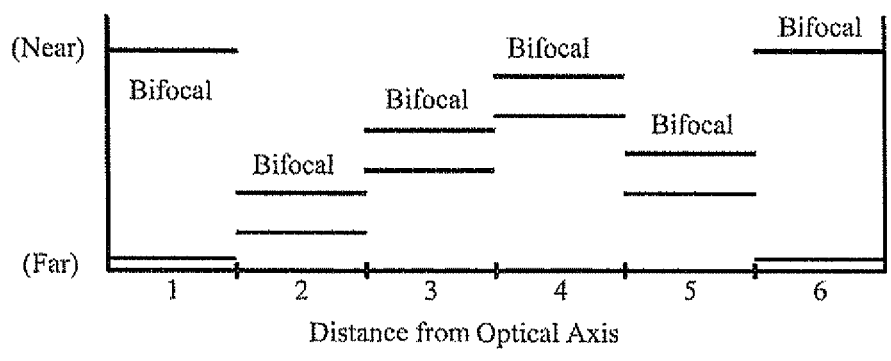
FIG. 16 is a plot of IOL power versus distance from optical axis for another IOL having six regions.

FIG. 16 shows power of an IOL embodiment in which power in the intermediate regions forms a "n" shape as a function of distance from the central region, and in which all six regions include a diffraction pattern so that each region provides two foci. The IOLs of FIGS. 14 and 16 provide improved vision at distances that decrease from the far focus, and light dims, down to objects at distances of the intermediate focal lengths associated with region 3 or 4, and then in still darker conditions where near and far vision are more desirable, more intensity (via light passing through the peripheral region) to the near and far foci.

The FIGS. 12-16 embodiments have in common providing some light intensity to mid range focus in intermediate light conditions, conditions where an eye iris expands to pass light through at least some of zones 2-5. The embodiments in FIGS. 12-16 also have in common providing, under lower light conditions, additional light intensity to either or both of a far and near focus, for example, when the iris expands to pass light through the peripheral zone 6. As with the other embodiments, these embodiments facilitate intermediate object distance vision in intermediate light conditions, while providing near and far distance vision under bright and low light conditions. In addition, the multiple intermediate foci may weaken the halo ring intensity associated with any particular region, thereby making halo less noticeable.

For IOLs like those in FIGS. 14-16 having a bifocal peripheral region, it may be desirable to change the power of the far focus of the peripheral regions that power minus 0.5 D, plus or minus 0.2 D. This can increase depth of field.

Figure 17:
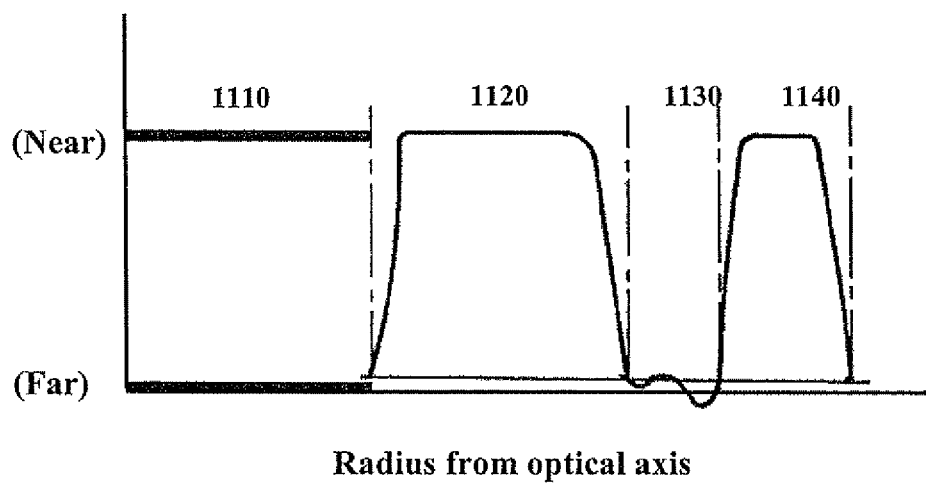
FIG. 17 is a plot of IOL power versus distance from optical axis for another IOL having four regions having sub-regions in which power is either constant or varies with radius from an optical axis.

FIG. 17 shows power of an IOL embodiment in which a central region 1110 comprises a diffractive pattern or phase plate configured to provide power to both near and far foci. The IOL further comprises intermediate regions 1120, 1130 and peripheral region 1140. Regions 1120, 1140 generally provide power for a near focus, but also include gradient portions having positive and negative slopes that are configured to also provide one or more intermediate foci between the near and far foci. Region 1130 generally provides power for a far focus, but also includes portions that provide power that is less than that needed to provide a far focus (e.g., a focus that has a focal length that is greater than the focal length required to focus light onto the retina of the eye). Other variations of power may be utilized to provide a desired combination of halo reduction, near/far power distribution with iris radius, insensitivity to decentration and tilt, and the like.

In certain embodiments, a method of making an IOL according to at least one of the above embodiments includes forming a central region and an outer region, the regions being disposed about an optical axis. The IOL may be formed using methods and means known in the art. For example, the IOL may be formed from a molding process. Alternatively, the IOL may be machined using a lath or similar such machine. In some embodiments, the IOL is molded and then one or both faces of an optic portion are machined, for example to form central, outer, intermediate, and/or peripheral regions according to embodiments of the present invention. In yet other embodiments, an optic is molded and/or machined to form central, outer, intermediate, or peripheral regions according to embodiments of the present invention. Subsequently, two or more haptics may be staked into the optic, the haptic being made of a different material that is generally stiffer than the material from which the optic is formed. Other forming methods and/or IOL features used in the art may be incorporated into the method of making an IOL. For example, a peripheral portion of the IOL may be structured to reduce glare and/or to reduce the migration of cells into an optic portion of the IOL.

In certain embodiments, a method of using an IOL according to an embodiment of the present invention comprises surgically removing a natural lens of a subject and inserting the IOL into the eye of the subject in the general location from which the natural lens was removed. For example, the method may include using a phacoemulsification machine to surgically remove the natural lens and leave at least portions of the surrounding capsular bag in tact. Subsequently, the IOL is inserted into the vacated capsular bag and generally centered within the capsular bag. The IOL may be inserted into the capsular bag using forceps or a specialized IOL inserter such as those know within the art. In some embodiments, the IOL is located in front of the capsular bag, for example, with the haptics extending into the ciliary body or ciliary muscle. In some embodiments, the natural lens is not removed and the IOL is a phakic IOL that acts in combination with the natural lens and cornea to provide vision. In other embodiments, the IOL is a supplemental IOL that is used in combination with another IOL, for example, where one of the IOL's is place in the capsular bag and the other IOL is placed in front of the capsular bag, in front of the iris, or implanted in a layer of the cornea of an eye.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

The invention claimed is:

1. An ophthalmic lens comprised of:
    a central region disposed about an optical axis comprised of a diffractive pattern with multifocal diffractive power comprised of a first base power and at least one additional power that is the sum of the first base power and the at least one additional power;
    more than one intermediate region disposed about the central region with each intermediate region comprised of at least one power between the first base power of the central region and any of the at least one additional power of the central region, wherein the power within each intermediate region remains constant, and wherein the power between each intermediate region increases from at or near the first base power of the central region, plateaus at or near the at least one additional power of the central region, and then decreases back down toward the first base power, as distance from the central region increases, such that the power of the more than one intermediate region forms an "n" shape as a function of distance from the central region; and
    a peripheral region disposed about the outermost intermediate region comprised of a diffractive pattern with multifocal diffractive power comprised of the first base power of the central region and the same additional power(s) as the central region.

2. The ophthalmic lens of claim 1, wherein the multifocal diffractive power of the central and peripheral regions is comprised of a first diffractive power and a second diffractive power for visible light, wherein the add power is equal to the difference between the first diffractive power and the second diffractive power.

3. The ophthalmic lens of claim 2, wherein the diffractive pattern of the central and peripheral regions has a primary diffractive order and a secondary diffractive order, the add power corresponding to light contained in the first diffractive order.

4. The ophthalmic lens of claim 3, wherein the first diffractive power is from a zeroth diffractive order of the diffractive pattern and the second diffractive power is from a first diffractive order of the diffractive pattern, or wherein the first diffractive power is from the first diffractive order, the second diffractive power is from a second diffractive order of the diffractive pattern, and the base power is produced by a combination of the first diffractive order and a refractive power of the central zone.

5. The ophthalmic lens of claim 1, wherein the more than one intermediate region is further comprised of a second base power, and at least one additional power that is the sum of the second base power and at least one add power.

6. The ophthalmic lens of claim 1, wherein at least one of the central region, the more than one intermediate region, and the outer region provides an extended depth of focus.

7. The ophthalmic lens of claim 1, wherein at least one surface deviates from spherical with aspheric terms designed to correct for the monochromatic aberrations.

8. The ophthalmic lens of claim 1, wherein the more than one intermediate region and/or peripheral region has a diffractive pattern designed to compensate for chromatic aberration.

9. An ophthalmic lens comprised of:
    a central region disposed about an optical axis comprised of a diffractive pattern with multifocal diffractive power comprised of a first base power and at least one additional power that is the sum of the first base power and the at least one additional power;
    more than one intermediate region disposed about the central region with each intermediate region comprised of at least one power between the first base power of the central region and any of the at least one additional power of the central region, wherein the power within each intermediate region remains constant, and wherein the power between each intermediate region decreases from at or near the at least one additional power of the central region, bottoms out at or near the first base power of the central region, and then increases toward the at least one additional power of the central region, as distance from the central region increases, such that the power of the more than one intermediate region forms a "u" shape as a function of the distance from the central region; and
    a peripheral region disposed about the outermost intermediate region comprised of a diffractive pattern with multifocal diffractive power comprised of the first base power of the central region and the same additional power(s) as the central region.

10. The ophthalmic lens of claim 9, wherein the multifocal diffractive power of the central and peripheral regions is comprised of a first diffractive power and a second diffractive power for visible light, wherein the add power is equal to the difference between the first diffractive power and the second diffractive power.

11. The ophthalmic lens of claim 10, wherein the diffractive pattern of the central and peripheral regions has a primary diffractive order and a secondary diffractive order, the add power corresponding to light contained in the first diffractive order.

12. The ophthalmic lens of claim 11, wherein the first diffractive power is from a zeroth diffractive order of the diffractive pattern and the second diffractive power is from a first diffractive order of the diffractive pattern, or wherein the first diffractive power is from the first diffractive order, the second diffractive power is from a second diffractive order of the diffractive pattern, and the base power is produced by a combination of the first diffractive order and a refractive power of the central zone.

13. The ophthalmic lens of claim 9, wherein the more than one intermediate region is further comprised of a second base power, and at least one additional power that is the sum of the second base power and at least one add power.

14. The ophthalmic lens of claim 9, wherein at least one of the central region, the more than one intermediate region, and the outer region provides an extended depth of focus.

15. The ophthalmic lens of claim 9, wherein at least one surface deviates from spherical with aspheric terms designed to correct for the monochromatic aberrations.

16. The ophthalmic lens of claim 9, wherein the more than one intermediate region and/or peripheral region has a diffractive pattern designed to compensate for chromatic aberration.

* * * * *